United States Patent [19]

Grosse-Bley et al.

[11] Patent Number: 5,347,042
[45] Date of Patent: Sep. 13, 1994

[54] OPTICALLY ACTIVE SULPHUR-CONTAINING AMINO ACID DERIVATIVES, THEIR PREPARATION, THEIR POLYMERISATION TO GIVE OPTICALLY ACTIVE POLYMERS AND THE USE THEREOF

[75] Inventors: Michael Grosse-Bley, Cologne; Bruno Bömer, Bergisch Gladbach; Rolf Grosser, Leverkusen; Dieter Arlt; Walter Lange, both of Cologne, all of Fed. Rep. of Germany

[73] Assignee: Bayer Aktiengesellschaft, Leverkusen, Fed. Rep. of Germany

[21] Appl. No.: 897,196

[22] Filed: Jun. 11, 1992

[30] Foreign Application Priority Data

Jun. 22, 1991 [DE] Fed. Rep. of Germany ........ 4120695

[51] Int. Cl.$^5$ ............................................ C07C 323/41
[52] U.S. Cl. ..................... 560/153; 548/200; 548/201; 560/16; 560/125; 564/154; 526/304
[58] Field of Search ........................ 560/153, 16, 125; 514/549

[56] References Cited

FOREIGN PATENT DOCUMENTS

| 0379917 | 8/1990 | European Pat. Off. . |
| 3706890 | 3/1987 | Fed. Rep. of Germany . |
| 40-10571 | 5/1965 | Japan ..................... 564/153 |

OTHER PUBLICATIONS

Chemical Abstracts, vol. 69, No. 9, 36430d Aug. 26, 1968.
Chemical Abstracts, vol. 99, No. 7, 53714m Aug. 15, 1983.
G. Blaschke et al., "Polymers Aminosäurederivate als optisch aktive Adsorbentien", Chemische Berichte, vol. 109 (1976) pp. 1967–1975.
K. Harada et al., "Syntheses of alpha–Amino Acid Menthyl Esters", Bull. Chem. Soc. Jpn. vol. 37 (1964) pp. 191–194.
B. B. Wheals, "Chemically bonded phases for liquid chromatography . . . ", J. Chromatography, vol. 107 (1975) pp. 402–406.
H. Engelhardt et al., "Polymer Encapsulated Stationary Phases . . . ", Chromatographie vol. 27 (1989) pp. 535–543.
Chemical Abstracts, Chemical Substance Index, vol. 76, p. 2164cs (1972).
Chemical Abstracts Service Registry Handbook, Number Section, 1974 Supplement, p. 36RC:45159-22-6 (1976).

Primary Examiner—Richard L. Raymond
Assistant Examiner—Scott C. Rand
Attorney, Agent, or Firm—Sprung Horn Kramer & Woods

[57] ABSTRACT

The invention relates to new optically active sulphur-containing amino acid derivatives, a process for their preparation, their polymerisation to give optically active polymers and the use of these optically active polymers as adsorbents for chromatographic separation of racemates into enantiomers.

5 Claims, No Drawings

OPTICALLY ACTIVE SULPHUR-CONTAINING AMINO ACID DERIVATIVES, THEIR PREPARATION, THEIR POLYMERISATION TO GIVE OPTICALLY ACTIVE POLYMERS AND THE USE THEREOF

The invention relates to new optically active sulphur-containing amino acid derivatives, a process for their preparation, their polymerisation to give optically active polymers and the use of these optically active polymers as adsorbents for chromatographic separation of racemates into enantiomers.

The separation of enantiomer mixtures into the enantiomers has gained ever more importance in recent years, because it has been found that the enantiomers of biologically active racemates can differ widely in their actions and side effects. There is therefore a great interest in the isolation of the individual enantiomers of biologically active racemates or enantiomer mixtures.

The most diverse adsorbents for chromatographic separation of racemates have already been proposed. The polymeric (meth)acrylic acid derivatives of optically active amino compounds described, for example in them. Ber. 109 (1976), 1967 or EP-A 379,917 have so far proved to be very advantageous adsorbents here, if appropriate in immobilised form on inorganic supports.

It has now been found, surprisingly, that amino acid derivatives which are derived from sulphur-containing amino acids lead, in combination with specific ester and amide radicals, in particular with sterically bulky and rigid ester or amide radicals, to very interesting new optically active adsorbents. It is to be found, completely unexpectedly, that a sulphur atom in the amino acid component significantly improves the separation properties for many separation problems compared with a pure hydrocarbon radical. The solubility of the monomers is also influenced favourably.

A number of active compound racemates, for example, can be separated considerably better on the sulphur-containing separation materials according to the invention than on the adsorbents known from the prior art.

The invention therefore relates to optically active sulphur-containing amino acid derivatives of the formula (I)

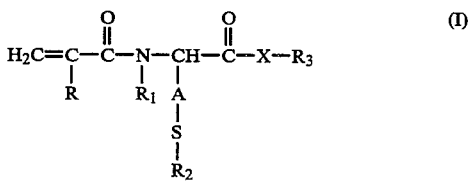

in which

R represents hydrogen, methyl or fluorine, $R_1$ represents hydrogen or $C_1$–$C_4$-alkyl, or together with $R_2$ forms a methylene group or a dimethylene group, which can be mono- or disubstituted by $C_1$–$C_4$-alkyl, $R_2$ represents a straight-chain, branched or cyclic alkyl radical having up to 10 C atoms, $C_6$–$C_{14}$-aryl,

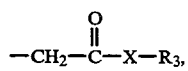

$C_2$–$C_{10}$-acyl or optionally substituted benzoyl or benzyl, or together with $R_1$ forms a bridge described for that radical, $R_3$ represents a straight-chain, branched or cyclic alkyl radical having up to 20 C atoms, which is optionally mono-, di- or trisubstituted by halogen, alkoxy having 1 to 4 C atoms, aralkoxy having 7 to 16 C atoms or aryl having 6 to 10 C atoms, and preferably represents a $C_{10}$-terpenyl radical, an adamantyl radical or a decahydronaphthyl radical, X denotes oxygen or an $NR_4$ group, in which $R_4$ represents hydrogen or $C_1$–$C_4$-alkyl, or together with $R_3$ forms a nitrogen-containing 5- to 7-membered ring, which can be mono- or di-$C_1$–$C_4$-alkyl- or -$C_1$–$C_6$-alkoxycarbonyl-substituted, and A represents a methylene or dimethylene group which is optionally mono- or di-$C_1$–$C_4$-alkyl-substituted, Preferred compounds of the formula (I) are those in which R represents hydrogen, methyl or fluorine, $R_1$ denotes hydrogen or methyl, or together with $R_2$ forms a methylene group, which can be mono- or dimethyl- or mono-tertiary butyl-substituted, or a dimethylene group, $R_2$ represents alkyl having up to 8 C atoms, phenyl or

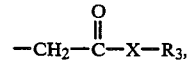

or together with $R_1$ forms a bridge described for that radical, $R_3$ represents a $C_{10}$-terpenyl radical, an adamantyl radical or a decahydronaphthyl radical, or represents an alkyl radical or cycloalkyl radical having in each case up to 12 C atoms, which is optionally mono- or disubstituted by $C_6$–$C_{10}$-aryl, $C_1$–$C_4$-alkoxy, $C_3$–$C_{12}$-cycloalkyl or halogen, it being possible for the aryl and cycloalkyl radicals mentioned to be substituted again in turn by $C_1$–$C_4$-alkyl, X denotes oxygen or an $NR_4$ group, in which $R_4$ represents hydrogen or $C_1$–$C_4$-alkyl, or together with $R_3$ forms a nitrogen-containing 5- to 7-membered ring, which can optionally be mono- or di-$C_1$–$C_4$-alkyl- or -$C_1$–$C_6$-alkoxycarbonyl-substituted, and A represents a methylene, dimethylmethylene or a dimethylene unit.

The optically active amino acid derivatives are preferably derived from optically active sulphur-containing amino acids, such as, for example, cysteine, penicillamine, or homocysteine. Compounds which are of particular interest for this purpose are those in which the SH function is alkylated, for example S-methyl-cysteine, S-benzyl-cysteine, S-methyl-penicillamine, methionine, ethionine or butionine, or acylated, for example S-acetyl-cysteine, or alkoxycarbonylmethylated, for example S-menthoxycarbonylmethyl-cysteine, or bonded to the amino group via an ethylene bridge, for example thioproline, 2,2-dimethyl-thioproline, 5,5-dimethylthioproline or 2-tert.-butylthioproline.

The use of optically active radicals, for example of the 1-phenylethyl, 1-(1-naphthylethyl), 1-(2-naphthylethyl), the d- or l-menthyl, d- or l-neomenthyl, d- or l-bornyl, d- or l-fenchyl or the d- or l-pinanyl radical, is particularly advantageous for $R_3$.

The optically active sulphur-containing amino acid derivatives of the formula (I) according to the invention are obtained by reaction of optically active sulphur-containing amino acid derivatives of the formula (II)

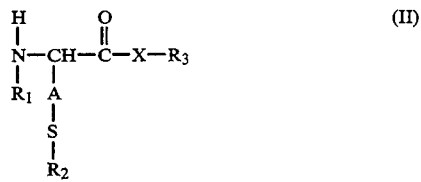

in which

R$_1$, R$_2$, R$_3$, A and X have the meaning given under formula (I), or acid addition products thereof, with acryloyl derivatives of the formula (III)

in which

R has the meaning given under formula (I) and

Y represents fluorine, chlorine or bromine, or represents the radical

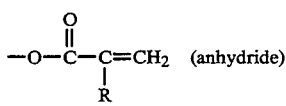

if appropriate in the presence of an acid-binding agent in inert organic solvents.

The optically active sulphur-containing amino acid derivatives of the formula (II) used as starting compounds are known or can be prepared by processes which are known per se (see Bull. Chem. Soc. Jpn. 37 (1964), 191).

Suitable acid addition compounds of the sulphur-containing amino acids to be used as starting substances are salts of these amino acids with inorganic or organic acids. Mineral acids, such as hydrochloric acid, hydrobromic acid, sulphuric acid or phosphoric acid, or organic acids, such as acetic acid, trifluoroacetic acid or methane-, ethane-, benzene- or toluenesulphonic acid, are preferred.

Suitable solvents are all the organic solvents which are inert under the reaction conditions. Hydrocarbons, such as toluene or petroleum ether, or halogenohydrocarbons, such as methylene chloride, dichloroethane or trichloroethylene, or ethers, such as tert.-butyl methyl ether, are preferred.

Possible acid-binding agents are, above all, the customary inorganic or organic bases; alkali metal or alkaline earth metal hydroxides, such as sodium, potassium, lithium, calcium or barium hydroxide, alkali metal or alkaline earth metal carbonates, such as sodium or potassium carbonate or sodium bicarbonate, alkali metal alcoholates, such as sodium methylate or ethylate or potassium methylate, ethylate or tert.-butylate, or amines, such as triethylamine or pyridine, are preferably used.

The reaction of the acryloyl derivatives of the formula (III) with the sulphur-containing amino acid derivatives of the formula (II) is preferably carried out at temperatures from −78° to +100° C., in particular from −20° to +60° C.

The invention also relates to the optically active polymers and copolymers which are obtainable by polymerisation or copolymerisation of the optically active sulphur-containing acryloylamino acid derivatives of the formula (I) and which contain at least 40 mol %, preferably at least 50 mol %, of structural units of the formula (IV)

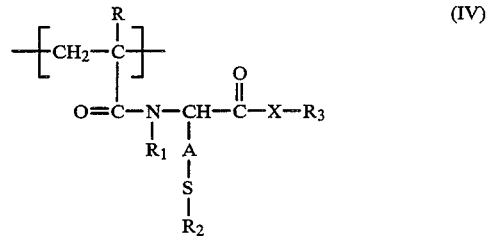

in which

R, R$_1$, R$_2$, R$_3$, A and X have the meaning given under formula (I).

The optically active polymers of the formula (IV) according to the invention are preferably in the form of crosslinked insoluble but swellable bead polymers or in a form bonded to finely divided inorganic carrier materials, such as, for example, silica gel. They can also be prepared as linear polymers which are soluble in suitable organic solvents. It is furthermore possible for different sulphur-containing acryloylamino acid derivatives of the formula (I) according to the invention to be copolymerized and for 0.1 to 60, preferably 0.1 to 20 mol % of other copolymerisable monomers to be incorporated into the polymers.

The crosslinked polymers are preferably in the form of small particles (beads) having a particle diameter of 5 to 200 μm. They are prepared, for example, by suspension polymerisation of the optically active sulphur-containing acryloylamino acid derivatives of the formula (I) with 0.5 to 50 mol %, preferably 1 to 30 mol %, particularly preferably 3 to 20 mol % (based on the total amount [mol] of the monomers employed) of a suitable crosslinking agent in a manner which is known per se.

The degree of swelling of the (bead) polymers can be adjusted by customary methods by the nature and amount of the crosslinking agents.

(Bead) polymers having a degree of swelling (Q) of 1.1 to 12.0, preferably 2.0 to 8.0, have proved suitable for use in practice.

The degree of swelling Q is determined as follows:

$$Q = \frac{\text{polymerisation volume (swollen)}}{\text{polymerisation volume (unswollen)}}$$

Possible crosslinking agents are compounds which contain at least two polymerisable vinyl groups. Preferred crosslinking agents are alkanediol diacrylates, such as 1,6-hexanediol diacrylate, 1,4-butanediol diacrylate, 1,3-propanediol diacrylate or 1,2-ethylene glycol diacrylate, or alkanediol dimethacrylates such as 1,4-, 1,3- or 2,3-butanediol dimethacrylate, 1,3-propanediol dimethacrylate or 1,2-ethylene glycol dimethacrylate, aromatic divinyl compounds, such as, for example, divinylbenzene, divinylchlorobenzene or divinyltoluene, dicarboxylic acid divinyl esters, such as divinyl adipate, divinyl benzenedicarboxylate or divinyl terephthalate, or N,N'-alkylenediacrylamides, such as N,N'-methylenediacrylamide, N,N'-ethylenediacrylamide, N,N'-methylenedimethacrylamide, N,N'-ethylenedimethacrylamide or N,N-dimethyl-ethylenediacrylamide.

Possible agents which form free radicals are the customary agents which form free radicals. Peroxides, such as, for example, dibenzoyl peroxide, dilauroyl peroxide or di-orthotolyl peroxide, peresters, such as tert.-butyl perpivalate or tert.-butyl peroctanoate, or azo compounds, such as, for example, azobisisobutyronitrile (AIBN) are preferred. Mixtures of different agents which form free radicals can also be used.

The polymerisation components are dissolved in a water-immiscible organic solvent, preferably an aliphatic or aromatic hydrocarbon, such as hexane, heptane, isodecane, benzene or toluene, a halogenohydrocarbon, such as methylene chloride, chloroform, carbon tetrachloride or 1,2-dichloroethane, an ester, such as ethyl acetate, butyl acetate or dialkyl carbonates, or a water-insoluble ketone, such as methyl isobutyl ketone or cyclohexanone.

The organic phase is uniformly distributed in the aqueous solution of a protective colloid, preferably in an aqueous solution of polyvinyl alcohol, polyvinylpyrrolidone or a copolymer of methacrylic acid and methyl methacrylate, with the aid of an effective stirrer. About 1 to 20, preferably 2 to 10 parts by weight of aqueous phase are used per part by weight of organic phase. The polymerisation mixture is heated at temperatures of 30° C. to 100° C., preferably at 40° C. to 80° C., in an inert gas atmosphere, preferably under nitrogen, while stirring. The polymerisation time is between 2 and 24, preferably 4 and 12 hours. The copolymer obtained in this manner is separated from the liquid phase by filtration, purified by thorough washing with water and with organic solvents, such as methanol, ethanol, benzene, toluene, methylene chloride, chloroform or acetone and then dried.

For analytical uses in particular, the optically active polymers according to the invention are preferably employed in a form bonded to finely divided inorganic carriers. Such optically active chromatography phases can be prepared, for example, by the processes described in DE-A 3,706,890.

Polymerisation of the optically active sulphur-containing amino acid derivatives of the formula (I) in the presence of silica gel vinyl phases, which are obtainable by the method of B. B. Wheals, J. Chromatogr. 107 (1975), 402 and H. Engelhardt et al., Chromatographia 27 (1989), 535, or of silica gel diol phases which have been esterified with (meth)acrylic acid is preferred. This polymerisation can be carried out in the absence of solvents or in the presence of solvents or of precipitating agents for the sulphur-containing poly-N-acryloylamide derivatives. The agents which form free radicals and are used for the preparation of the bead polymers can also be employed as initiators.

The polymer-modified silica gels preferably contain 1 to 40% by weight, in particular 5 to 30% by weight, of optically active monomer (I), based on the total weight. They are washed intensively with solvents for the polymer and dried in vacuo.

Mixtures of two or more of the sulphur-containing N-acryloyl-amino acid derivatives according to the invention, if appropriate also with other copolymerisable monomers, can of course also be employed here.

The invention furthermore relates to the use of the sulphur-containing polyacrylamides according to the invention, as such or in crosslinked form or in a form bonded to silica gel, for chromatographic separation of racemic mixtures into the optical antipodes. The polymers according to the invention have proved to be particularly suitable for chromatographic separation of hexahydrocarbazole derivatives, such as, for example, 3-r-(4-fluorophenylsulphonamido)-9-(2-carboxyethyl)-1,2,3,4,4a,9a-hexahydrocarbazole, and of N-3,5-dinitrobenzoyl-derivatised amino acids, benzodiazepines, such as oxazepam, arylpropionic acids and their amides, such as ketoprofen and ibuprofenamide, dihydropyridines, such as, for example, 5-methyl 1,4-dihydro-2,6-dimethyl-4-(2-trifluoromethylphenyl)pyridine-3,5-dicarboxylate, and trifluoroanthrylethanol.

The composition of the mobile phase can be chosen and optimised in the customary manner according to the nature and properties of the racemate to be separated. The sulphur-containing polyacrylamides according to the invention bonded in the silica gel can be employed for chromatographic racemate separations under HPLC conditions.

The ability of the polymers to separate racemates is expressed by the capacity ratios ($k'_{1(2)}$ values) for the two enantiomers (1) and (2) and the resulting enantioselectivity value $\alpha$. These chromatographic parameters are defined as follows:

$$\text{Capacity ratio } k'_{1(2)} = \frac{t_{1(2)} - t_0}{t_0}$$

$$\text{Enantioselectivity } \alpha = \frac{k'_2}{k'_1}$$

$t_0$ = dead time of the column $t_{1(2)}$ = Retention time of the enantiomer 1 eluted first or the enantiomer 2 eluted later.

The preparative separation of racemic mixtures into their optical antipodes using the polymers according to the invention is preferably carried out by column chromatography. For this purpose, it is particularly advantageous to carry out the chromatographic separation using bead polymers having a certain particle size distribution; good separation efficiencies are obtained with bead polymers having a particle size distribution of 5 to 200 μm, preferably 15 to 100 μm.

The operating method of column chromatography separation is known. The polymer is usually suspended in the mobile phase and the suspension is introduced into a glass column. After the mobile phase has drained out, the racemate to be separated, dissolved in the mobile phase, is applied to the column. The column is then eluted with the mobile phase and the enantiomers in the eluate are detected photometrically or polarimetrically by means of suitable flow-through cells.

Organic solvents or solvent mixtures which swell the polymer employed as the adsorbent and dissolve the racemate to be separated are usually used as the mobile phase. Examples which may be mentioned are: hydrocarbons, such as benzene, toluene or xylene, ethers, such as diethyl ether, tert.-butyl methyl ether, dioxane or tetrahydrofuran, halogenohydrocarbons, such as methylene chloride or chloroform, acetone, acetonitrile or ethyl acetate, alcohols, such as methanol, ethanol, n-propanol, isopropanol or n-butanol, or mixtures of the solvents mentioned. Mixtures of toluene with tetrahydrofuran, dioxane or isopropanol have proved to be particularly suitable.

EXAMPLES

I. PREPARATION METHOD FOR THE OPTICALLY ACTIVE SULPHUR-CONTAINING N-ACRYLOYLAMINO ACID DERIVATIVES (I) (MONOMERS)

Example 1

8.5 g (84 mmol) of triethylamine are added to a solution of 23 g (80 mmol) of L-methionine d-menthyl ester in 700 ml of methylene chloride at 0° C. A solution of 8.5 g (82 mmol) of methacryloyl chloride in 50 ml of methylene chloride is then added dropwise at −10° C. The mixture is allowed to come to room temperature and is then washed with water, 1N hydrochloric acid and saturated sodium bicarbonate solution. The organic phase is dried over magnesium sulphate. After the solvent has been distilled off, the residue is recrystallised from n-heptane.

24 g (85%) of N-methacryloyl-L-methionine d-menthyl ester are obtained in the form of colourless crystals of melting point: 47° C. Optical rotation $[\alpha]_D$: +66.2° (c=1, CHCl$_3$).

Instead of by crystallisation, the residue can also be purified by chromatography on silica gel using hexane:ethyl acetate=3:1 as the eluent.

Instead of the free amino ester the corresponding hydrochloride can also be employed with the same success. The amount of triethylamine must then be doubled.

Example 2

8.1 g (80 mmol) of triethylamine are added to a solution of 21.4 g (75 mmol) of L-methionine (1S)-bornyl ester in 650 ml of methylene chloride at 0° C. A solution of 8.7 g (80 mmol) of fluoroacryloyl chloride in 50 ml of methylene chloride is then added dropwise at −10° C. The mixture is allowed to come to room temperature. It is then washed with water, 1N hydrochloric acid and saturated sodium bicarbonate solution. The organic phase is dried over magnesium sulphate. After the solvent has been distilled off, the residue is purified by flash chromatography on silica gel using petroleum ether:ethyl acetate=3:1 as the eluent.

17 g (63%) of N-fluoroacryloyl-L-methionine (1S)-bornyl ester are obtained as a colourless oil having an optical rotation $[\alpha]_D$= +2.0° C. (c=1, CHCl$_3$).

Example 3

3.5 g (35 mmol) of triethylamine are added to a solution of 8.1 g (30 mmol) of (R)-thioproline 1-menthylamide in 100 ml of methylene chloride at 0° C. A solution of 3.1 g (34 mmol) of acryloyl chloride in 20 ml of methylene chloride is then added dropwise at −10° C. The mixture is allowed to come to room temperature.

Working up is as described under Example 1. 6 g (64%) of N-acryloyl-(R)-thioproline 1-menthylamide are obtained in the form of colourless crystals of melting point 149° C. (from n-heptane). Optical rotation $[\alpha]_D$: −184.5° (c=1, CHCl$_3$).

N-(meth)acryloylamino acid derivatives are obtained from the optically active sulphur-containing amino acid derivatives shown in Table 1 in the manner described. The table also contains the yields, melting points and optical rotations of the products.

TABLE I

Monomer synthesis

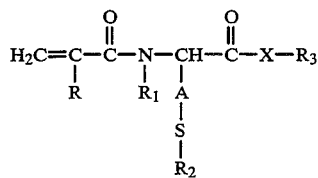

(I)

| Example | Radical groups | Starting compound | Product | M.p. (°C.) | $[\alpha]_D$ (c = 1, CHCl$_3$) | Yield (% of theory) |
|---|---|---|---|---|---|---|
| 1 | R = CH$_3$, R$_1$ = H<br>R$_2$ = CH$_3$, R$_3$ = d-menthyl<br>X = O, A = CH$_2$—CH$_2$ | | compare text | | | |
| 2 | R = F, R$_1$ = H<br>R$_2$ = CH$_3$, R$_3$ = (1S)-bornyl<br>X = O, A = CH$_2$—CH$_2$ | | " | | | |
| 3 | R = H, R$_1$-R$_2$ = CH$_2$<br>R$_3$ = l-menthyl,<br>X = NH, A = CH$_2$ | | " | | | |
| 4 | R = H, R$_1$ = H<br>R$_2$ = CH$_3$, R$_3$ = l-menthyl<br>X = O, A = CH$_2$—CH$_2$ | L-methionine l-menthyl ester | N-acryloyl-L-methionine l-menthyl ester | 87 | −19.5° | 90 |
| 5 | R = H, R$_1$-R$_2$ = CH$_2$<br>R$_3$ = d-menthyl<br>X = O, A = CH$_2$ | (R)-thioproline d-menthyl ester | N-acryloyl-(R)-thioproline d-menthyl ester | oil | −29.5° | 72 |
| 6 | R = H, R$_1$-R$_2$ = CH$_2$<br>R$_3$ = l-menthyl<br>X = O. A = CH$_2$ | (R)-thioproline l-menthyl ester | N-acryloyl-(R)-thioproline l-menthyl ester | oil | −115.3° | 90 |
| 7 | R = CH$_3$, R$_1$ = H<br>R$_2$ = CH$_3$, R$_3$ = $^t$Bu<br>X = O, A = CH$_2$CH$_2$ | L-methionine-tert.-butyl ester | N-methacryloyl-L-methionine-tert.-butyl ester | 58 | +45.0° | 91 |
| 8 | R = CH$_3$, R$_1$ = H<br>R$_2$ = CH$_3$, R$_3$ = l-menthyl,<br>X = O, A = CH$_2$CH$_2$ | L-methionine l-menthyl ester | N-methacryloyl-L-methionine l-menthyl ester | 80 | −27.3° | 81 |
| 9 | R = CH$_3$, R$_1$ = H | L-methionine | N-methacryloyl- | 161 | −68.3° | 65 |

TABLE I-continued

Monomer synthesis $$H_2C=\underset{R}{C}-\underset{}{\overset{O}{\overset{\|}{C}}}-\underset{R_1}{N}-\underset{\underset{\underset{\underset{R_2}{|}}{S}}{\underset{|}{A}}}{CH}-\overset{O}{\overset{\|}{C}}-X-R_3 \qquad (I)$$

| Example | Radical groups | Starting compound | Product | M.p. (°C.) | $[\alpha]_D$ (c = 1, CHCl$_3$) | Yield (% of theory) |
|---|---|---|---|---|---|---|
|  | $R_2 = CH_3, R_3 = $ l-menthyl, $X = NH, A = CH_2CH_2$ | l-methylamide | L-methionine l-menthylamide |  |  |  |
| 10 | $R = H, R_1 = H, R_2 = CH_3$, $R_3 = $ l-menthyl $X = NH, A = CH_2-CH_2$ | L-methionine l-menthylamide | N-acryloyl-L-methionine l-menthylamide | 167 | −76.1° | 63 |
| 11 | $R = CH_3, R_1 = H$ $R_2 = CH_3, R_3 = $ d-menthyl $X = NH, A = CH_2-CH_2$ | L-methionine d-menthylamide | N-methacryloyl-L-methionine d-menthylamide | 192 | +38.4° | 85 |
| 12 | $R = H, R_1 = H$ $R_2 = CH_3, R_3 = $ d-menthyl, $X = NH, A = CH_2CH_2$ | L-methionine d-menthylamide | N-acryloyl-L-methionine d-menthylamide | 209 | +19.1° | 55 |
| 13 | $R = CH_3, R_1-R_2 = CH_2$ $R_3 = $ l-menthyl, $X = NH$ $A = CH_2$ | (R)-thioproline l-menthylamide | N-methacryloyl-(R)-thioproline l-menthylamide | 154 | −195.3° | 65 |
| 14 | $R = H, R_1 = H$ $R_2 = CH_3, R_3 = $ d-menthyl $X = O, A = CH_2-CH_2$ | L-methionine d-menthyl ester | N-acryloyl-L-methionine d-menthyl ester | 74 | +83.6° | 67 |
| 15 | $R = H, R_1-R_2 = CH_2$ $R_3 = $ d-menthyl, $X = NH, A = CH_2$ | (R)-thioproline d-menthylamide | N-acryloyl-(R)-thioproline d-menthylamide | 110 | −78.8° | 59 |
| 16 | $R = CH_3, R_1 = H$ $R_2 = CH_2CH_3, R_3 = $ d-menthyl, $X = NH, A = CH_2CH_2$ | D-ethionine d-menthylamide | N-methacryloyl-D-ethionine d-menthylamide | 127 | −73.7° | 66 |
| 17 | $R = CH_3, R_1 = H$ $R_2 = CH_2CH_3, R_3 = $ l-menthyl, $X = NH, A = CH_2CH_2$ | D-ethionine l-menthylamide | N-methacryloyl-D-ethionine l-menthylamide | 178 | −28.3° | 44 |
| 18 | $R = CH_3, R_1 = H$ $R_2 = CH_3, R_3 = $ (S)-phenylethyl $X = NH, A = CH_2CH_2$ | L-methionine (S)-phenylethylamide | N-methacryloyl-L-methionine (S)-phenylethyl amide | 137 | −52.6° | 77 |
| 19 | $R = CH_3, R_1 = H, R_2 = CH_3$, $R_3 = $ d-neomenthyl $X = NH, A = CH_2CH_2$ | L-methionine d-neomenthylamide | N-methacryloyl-L-methionine d-neomenthylamide | 170 | +9.1° | 83 |
| 20 | $R = CH_3, R_1 = H, R_2 = CH_3$, $R_3 = $ (R)-phenylethyl $X = NH, A = CH_2CH_2$ | L-methionine (R)-phenylethylamide | N-methacryloyl-L-methionine (R)-phenylethyl amide | 121 | +7.8° | 56 |
| 21 | $R = CH_3, R_1 = H, R_2 = CH_3$, $R_3 = $ phenyl, $X = NH$ $A = CH_2CH_2$ | L-methionine anilide | N-methacryloyl-L-methionine anilide | 117 | −29.8° | 88 |
| 22 | $R = CH_3, R_1 = H, R_2 = CH_3$. $R_3 = $ 3,5-dimethylphenyl, $X = NH$ $A = CH_2CH_2$ | L-methionine 3,5-dimethylanilide | N-methacryloyl-L-methionine 3,5-dimethylanilide | 114 | −18.1° | 80 |
| 23 | $R = CH_3, R_1 = H, R_2 = CH_3$, $R_3 = $ 3-pentyl $X = NH, A = CH_2CH_2$ | L-methionine 3-pentylamide | N-methacryloyl-L-methionine 3-pentylamide | 128 | −21.8° | 66 |
| 24 | $R = CH_3, R_1 = H, R_2 = CH_3$, $R_3 = $ l-menthyl $X = NH, A = CH_2$ | S-methyl-L-cysteine l-menthylamide | N-methacryloyl-S-methyl-L-cysteine l-menthylamide | 155 | −81.4° (MeOH) | 63 |
| 25 | $R = H, R_1-R_2 = CH_2$ $R_3 = $ (S)-phenylethyl $X = NH, A = CH_2$ | (R)-thioproline (S)-phenylethylamide | N-acryloyl-(R)-thioproline (S)-phenylethylamide | 112 | −164.7° | 30 |
| 26 | $R = CH_3, R_1 = H, R_2 = CH_3$, $R_3 = CH_2CH_3$ $X = NCH_2CH_3, A = CH_2CH_2$ | L-Methionin-diethylamide | N-Methacryloyl-L-methionin-diethylamide | oil | −3,5° | 58 |

II. POLYMERISATION OF THE OPTICALLY ACTIVE SULPHUR-CONTAINING AMINO ACID DERIVATIVES (I)

1. Preparation in a Form Bonded to Silica Gel 3.0 g of vinyl-silica gel (prepared from silica gel Si 100/5µ or 10µ by the method of H. Engelhardt et al., Chromatographia 27 (1989) 535) are dissolved or suspended in 25 ml of toluene with 6.0 g of sulphur-containing amino acid derivative I and 100 mg of azobisisobutyronitrile. The apparatus is evacuated and filled with nitrogen three times, while stirring with a magnet. The mixture is then polymerised at 80° C. for 45 minutes. After addition of 100 mg of 2,6-di-tert.-butyl-4-methylphenol the mixture is cooled rapidly to room temperature. The silica gel is filtered off with suction over a G4 frit and stirred twice in chloroform, once in toluene and once in isopropanol for 15 minutes each time, being filtered off with suction in between. The silica gel is then dried in vacuo (<0.005 atmosphere) at room temperature.

The sulphur-containing amino acid derivatives polymerised, the yields of optically active silica gel, the nitrogen content thereof and, from this, the content of bonded polymer are summarised in the following Table II.

Similar results of bonded optically active polymer are obtained if silica gel diol esterified with methacrylic anhydride is used instead of vinyl-silica gel.

TABLE III

| | Bead polymers | | | | |
|---|---|---|---|---|---|
| Example | Monomer according to Example No. | Yield (g) | Particle size (μm) | $V_s$ (ml/g) | $V_q$ (ml/g) |
| 8B | 8 | 12.0 | 15–60 | 1.9 | 5.1 |
| 9B | 9 | 12.1 | 10–50 | 1.7 | 5.9 |
| 10B | 10 | 11.4 | 10–30 | 1.9 | 6.7 |
| 11B | 11 | 11.7 | 15–60 | 2.0 | 5.7 |
| 18B | 18 | 13.6 | 10–60 | 1.8 | 4.4 |
| 19B | 19 | 11.5 | 20–90 | 1.9 | 4.9 |
| 20B | 20 | 11.7 | 15–85 | 1.8 | 4.6 |
| 23B | 23 | 11.0 | 15–85 | 1.9 | 4.4 |

Use of the Optically Active Polymers of Sulphur-Containing Amino Acid Derivatives (I) as Adsorbents for Racemate Separation

TABLE II

| | | Silica gel phases | | |
|---|---|---|---|---|
| Example | Monomer according to Example No. | Yield (g) | N content (%) | Content of bonded polymer (% by weight) |
| 1A | 1 | 3.5 | 0.6 | 15.2 |
| 2A | 2 | 3.5 | 0.7 | 17.8 |
| 3A | 3 | 3.45 | 1.5 | 17.4 |
| 4A | 4 | 3.2 | 0.55 | 13.4 |
| 6A | 6 | 3.3 | 0.65 | 15.1 |
| 7A | 7 | 3.4 | 0.8 | 15.6 |
| 8A | 8 | 3.4 | 0.6 | 15.2 |
| 9A | 9 | 3.2 | 0.8 | 10.1 |
| 10A | 10 | 3.3 | 1.35 | 16.4 |
| 11A | 11 | 3.4 | 1.2 | 15.2 |
| 12A | 12 | 3.5 | 1.4 | 17.0 |
| 13A | 13 | 3.1 | 0.2 | 2.4 |
| 14A | 14 | 3.2 | 0.65 | 15.9 |
| 15A | 15 | 3.6 | 2.0 | 23.2 |
| 16A | 16 | 3.3 | 0.5 | 6.6 |
| 17A | 17 | 3.4 | 1.2 | 15.8 |
| 18A | 18 | 3.5 | 1.8 | 20.6 |
| 19A | 19 | 3.3 | 1.15 | 14.5 |
| 20A | 20 | 3.4 | 1.5 | 17.2 |
| 21A | 21 | 3.4 | 1.45 | 15.2 |
| 22A | 22 | 3.5 | 1.5 | 17.1 |
| 23A | 23 | 3.4 | 1.75 | 17.9 |
| 24A | 24 | 3.1 | 1.3 | 15.8 |

2. Preparation in the Form of Bead Polymers

A solution of 13.5 g of sulphur-containing amino acid derivative I, 1.5 g of ethylene glycol dimethacrylate and 0.3 g of azobisisobutyronitrile in 45 g of chloroform is dispersed in a solution of 5 g of polyvinyl alcohol in 130 ml of water, while stirring at 450 revolutions/min. The apparatus is evacuated and filled with nitrogen several times. Polymerisation is then carried out at 55° C. for 16 hours under nitrogen. The polymerisation mixture is then stirred into 2 to 3 l of water and, after the bead polymer has settled, the liquid phase is decanted. The bead polymer is freed from fine particles (polymer having a particle size of less than 10 μm) by suspending in water and decanting off the liquid phase 3 to 4 times and, after intensive washing with acetone, is dried to constant weight at 60° C.

The sulphur-containing amino acid derivatives used for the polymerisation, the yields in which the polymers were obtained, the particle size thereof and the volume of the resulting bead polymers in the dried ($V_s$) and swollen ($V_q$) state (swelling agent: toluene=T or toluene/tetrahydrofuran =3:2 v/v mixture=T/T) are summarised in the following Table III.

The following test racemates were used for the chromatographic separations:

Racemate No. 1: 3-r-(4-fluorophenylsulphonamido)-9-(2-carboxyethyl)-1,2,3,4,4a,9a-hexahydrocarbazole
Racemate No. 2: Oxazepam
Racemate No. 3: Ketoprofen
Racemate No. 4: 5-Methyl 1,4-dihydro-2,6-dimethyl-4-(2-trifluoromethylphenyl)pyridine-3,5-dicarboxylate
Racemate No. 5: N-3,5-dinitrobenzoylleucine
Racemate No. 6: Trifluoroanthrylethanol
Racemate No. 7: Ibuprofenamide The polymers bonded to silica gel were employed in steel columns (internal diameter: 4 mm; length: 25 cm). The columns were eluted with n-heptane/tetrahydrofuran mixtures: 1:1 (vol/vol)=eluting agent a, 1:2=eluting agent b. The flow rate of the mobile phase was 1 ml/min.

The bead polymers were employed in a glass column (internal diameter: 1.2 cm; bed height: 25–30 cm). The column was eluted with a toluene/tetrahydrofuran mixture 3:1 (vol/vol). The flow rate of the mobile phase was 0.5 ml/minute.

The results obtained in the chromatographic separation of the various tests racemates (enantioselectivity α and capacity ratio $k'_1$) and the eluting agents used are summarised in Table IV. An example is given here for the adsorbents according to the invention in comparison with the analogous sulphur-free phase (see EP-A 379,917). It is found that the sulphur-free norleucine phase is inferior to the sulphur-containing methionine phase according to the invention.

TABLE IV

| | Separation results from N-methacryloyl-L-methionine l-menthylamide (→ 9A) | | | Stationary phase from N-methacryloyl-L-norleucine l-menthylamide (EP 379,917) | | |
|---|---|---|---|---|---|---|
| | 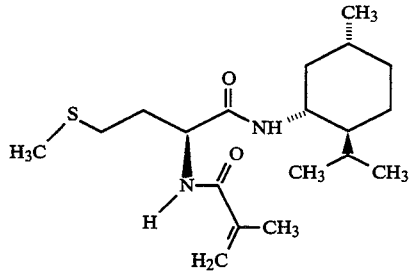 | | | 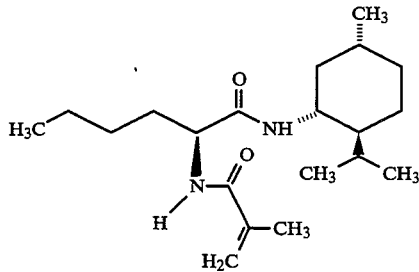 | | |
| Racemate | Eluent | k'₁ | alpha | Eluent | k' | alpha |
| No. 1 | Heptane:THF = 1:2 | 2.88 | 5.00 | no separation | | |
| No. 2 | Heptane:THF = 1:1 | 2.67 | 4.32 | Heptane:THF = 1:2 | 4.00 | 1.34 |
| No. 3 | Heptane:THF = 3:1 | 3.06 | 1.09 | no separation | | |
| No. 4 | Heptane:THF = 1:1 | 1.64 | 2.14 | Heptane:THF = 1:1 | 2.77 | 1.68 |
| No. 5 | Heptane:THF = 1:1 | 0.56 | 1.63 | Heptane:THF = 1:1 | 0.63 | 1.17 |
| No. 6 | Heptane:isopropanol = 10:1 | 1.33 | 1.26 | Heptane:isopropanol = 10:1 | 1.13 | 1.16 |
| No. 7 | Heptane:THF = 1:1 | 1.74 | 1.82 | Heptane:THF = 1:1 | 1.99 | 1.77 |

We claim:

1. An optically active sulphur-containing amino acid derivative of the formula

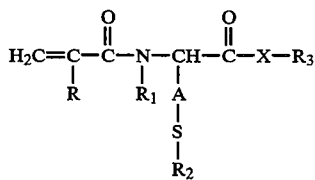

in which

R represents hydrogen, methyl or fluorine,
R₁ represents hydrogen or C₁–C₄-alkyl,
R₂ represents a straight-chain, branched or cyclic alkyl radical having up to 10 C atoms, or phenyl
R₃ represents a C₁₀-terpenyl radical, an adamantyl radical or a decahydronaphthyl radical, or represents a branched alkyl or cycloalkyl radical having from 2 to 20 C atoms, which is optionally mono-, di- or trisubstituted by halogen, alkoxy having 1 to 4 C atoms, or C₃–C₁₂-cycloalkyl, wherein the aryl and cycloalkyl radicals are optionally substituted by C₁–C₄-alkyl, and
A represents a methylene or dimethylene group which is optionally mono- or di-C₁–C₄-alkyl-substituted.

2. A compound according to claim 1, in which

R represents hydrogen, methyl or fluorine,
R₁ denotes hydrogen or methyl,
R₂ represents alkyl having up to 8 C atoms or phenyl
R₃ represents a C₁₀-terpenyl radical, an adamantyl radical or a decahydronaphthyl radical, or represents a branched alkyl or cycloalkyl radical having from 4 to 12 C atoms, which is optionally mono- or di-substituted by C₆–C₁₀-aryl, C₁–C₄-alkoxy, C₃–C₁₂-cycloalkyl or halogen, wherein the aryl and cycloalkyl radicals are optionally substituted by C₁–C₄-alkyl, and
A represents a methylene, dimethylmethylene, or dimethylene group.

3. A compound according to claim 1 wherein A is

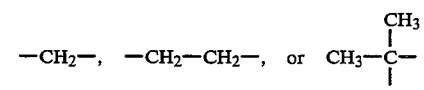

and R₂ is an alkyl or phenyl.

4. A compound according to claim 1, in which R₃ is tert-butyl or 3-pentyl.

5. A compound according to claim 1 of the formula

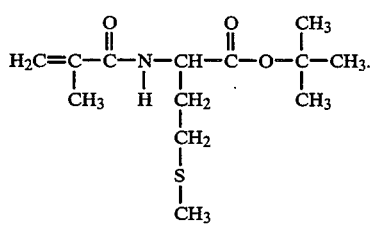

* * * * *

UNITED STATES PATENT AND TRADEMARK OFFICE
CERTIFICATE OF CORRECTION

PATENT NO. : 5,347,042
DATED : September 13, 1994
INVENTOR(S) : Grosse-Bley, et al.

It is certified that error appears in the above-identified patent and that said Letters Patent is hereby corrected as shown below:

Title Page  Insert -- U.S. PATENT DOCUMENTS
              3,615,624    1/1968   Smith et al.....430/657
              3,884,761    5/1975   Cowling.........435/180
              3,846,306   11/1974   Barker, et al...435/180
                                                          --

Col. 13, line 43   Delete " X " in the formula and substitute
                   -- 0 --

Col. 13, line 58   After " from " delete " 2 " and substitute
                   -- 4 --

Col. 13, line 60   After " 4 C atoms, " insert -- aralkoxy
                   having 7 to 16 C atoms, aryl having 6-10 C
                   atoms, --

Signed and Sealed this

Twenty-fifth Day of April, 1995

Attest:

BRUCE LEHMAN

*Attesting Officer*        *Commissioner of Patents and Trademarks*